United States Patent [19]

Cannon et al.

[11] Patent Number: 5,245,290
[45] Date of Patent: Sep. 14, 1993

[54] DEVICE FOR DETERMINING THE SIZE AND CHARGE OF COLLOIDAL PARTICLES BY MEASURING ELECTROACOUSTIC EFFECT

[75] Inventors: David W. Cannon, Attleboro Falls, Mass.; Richard W. O'Brien, Turramurra N.S.W., Australia

[73] Assignees: Matec Applied Sciences, Inc., Hopkinton, Mass.; Colloidal Dynamics, Sydney, Australia

[21] Appl. No.: 749,445

[22] Filed: Aug. 23, 1991

Related U.S. Application Data

[63] Continuation-in-part of Ser. No. 328,254, Feb. 27, 1989, Pat. No. 5,059,909.

[51] Int. Cl.[5] ............. G01R 29/12; G01N 15/02
[52] U.S. Cl. ............................... 324/457; 73/597; 73/865.5; 324/72; 324/453; 324/71.1
[58] Field of Search ............ 324/71.1, 452, 453, 324/457, 72; 73/584, 587, 589, 592, 596, 602, 865.5, 597

[56] References Cited

U.S. PATENT DOCUMENTS

| 3,633,415 | 1/1972 | Luce . | |
|---|---|---|---|
| 4,375,673 | 3/1983 | Lewis et al. . | |
| 4,497,208 | 2/1985 | Oja et al. . | |
| 4,552,019 | 11/1985 | Freeman | 73/584 |
| 4,633,714 | 1/1987 | Mazumder et al. . | |
| 4,679,439 | 7/1987 | Culkin . | |
| 4,907,453 | 3/1990 | Marlow et al. | 73/584 |

FOREIGN PATENT DOCUMENTS

WO8600707 1/1986 PCT Int'l Appl. .
WO8602727 5/1986 PCT Int'l Appl. .
1185898 3/1970 United Kingdom .

OTHER PUBLICATIONS

"Measurement of Suspended Particles by Quasi-Elastic Light Scattering", M. K. Mazumber, et al., pp. 327-341, Dec. 1983.
"Electro-Acoustic effects in a dilute suspension of spherical particles", R. W. O'Brien, J. Fluid Mech. Dec. 1988, vol. 190, pp. 71-86.
"The electroacoustic equations for a colloidal suspension", R. W. O'Brien, J. Fluid Mech. Dec. 1990, vol. 212, pp. 81-93.

Primary Examiner—Gerard R. Strecker
Assistant Examiner—Diep Do
Attorney, Agent, or Firm—Blum Kaplan

[57] ABSTRACT

An apparatus for determining the particle charge and size distribution of particles in suspensions of arbitrary concentration is provided. The apparatus includes a cell for application of an unsteady electric field or an unsteady mechanical force across the suspension of at least two different frequencies for accelerating the particles. The resulting acoustic wave generated by application of the electric field applied to the electrodes, or the electrical response and the acoustic pressure at the electrodes generated by application of the mechanical force is measured. Transducers convert the mechanical forces to electrical forces.

20 Claims, 6 Drawing Sheets

DEVICE FOR DETERMINING THE SIZE AND CHARGE OF COLLOIDAL PARTICLES BY MEASURING ELECTROACOUSTIC EFFECT

CROSS-REFERENCE TO RELATED APPLICATION

This application is a continuation-in-part of application Ser. No. 07/328,254, filed on Feb. 27, 1989 now, U.S. Pat. No. 5,059,909.

BACKGROUND OF THE INVENTION

This invention relates to a device for determining the size and charge of colloidal particles, and, in particular to a device for measuring the electrophoretic mobility of colloidal sols or suspensions of small particles in a liquid, such as blood, milk, paints, inks and slurries.

A device designed to determine the size distribution and the electric charge of the particles in a colloidal sol has many potential applications. The device is suitable for use in the paint industry for controlling the optical and flow properties of paints, since these quantities are sensitive to particle size and charge. Further, the device can be used to monitor the size of particles as the particles flow around a grinding circuit prior to sintering for forming a ceramic.

Although there are a number of commercial devices for determining the size and charge of particles on the market, these conventional devices employ optical techniques which are inoperative with concentrated, opaque suspensions that are usually encountered in industry. On the other hand, the instruments to be described herein are applicable to opaque suspensions, because the instruments determine particle size from the measurement of the electroacoustic effects, rather than light.

The instruments described herein determine size and charge of particles in accordance with the method described by Richard W. O'Brien in U.S. patent application Ser. No. 07/328,254 incorporated herein by reference (hereinafter referred to as "the O'Brien Method". In sum, the O'Brien Method determines the particle charge and size distribution of particles in suspensions of arbitrary concentration by applying at least one of an unsteady electrical field of at least two frequencies and an unsteady mechanical force of at least two different frequencies to the suspension to accelerate the particles. The resulting acoustic waves or electrical responses ("the electroacoustic effect") are measured at each application frequency. A quantity known as the "frequency dependent electrophoretic mobility" ($\mu$) of the particles is determined from the measurements and the size and charge are calculated from the frequency dependent mobility, which will also be referred to here as the "dynamic mobility". The O'Brien Method for determining the size and charge of colloidal particle involves a quantity, referred to as the "frequency dependent electrophoretic mobility".

Prior to describing the O'Brien Method and the instruments suitable for use, the definition of the "dynamic mobility" should be described.

DEFINITION OF DYNAMIC MOBILITY

A suspension can be subjected to a spatially uniform alternating electric field by applying an alternating voltage across a pair of parallel plate electrodes in contact with the suspension. In the region between the plates, the field will be spatially uniform. The electric field exerts a force on the particles, because they are electrically charged which causes the particles to move backwards and forwards at the frequency of the applied voltage. As the particles move, they generate microscopic sound waves. These microscopic sound waves superpose and result in a macroscopic sound wave field in the suspension.

In view of this, there will be a bulk motion of the suspension backwards and forwards between the plates. This in turn will affect the particle motion which will be explained in greater detail below. However, assume that the suspension is so dilute that the sound waves are very weak, therefore the sound waves effect on the particle motion can be neglected. In this case, the particle motion is the same as if each particle were alone in an infinite liquid subjected to a spatially uniform ambient field.

The curves in FIG. 1 represent the electric field strength and the average particle velocity as a function of time. The solid line is the electric field and the dashed line is the velocity. The quantities E and V in FIG. 1 ar the amplitude of the electric field and the particle velocity, respectively. In general, a time delay will occur between the electric field and the particle velocity due to inertial forces in the particle and the liquid. This time delay, which depends on the frequency and the particle mass, is denoted in FIG. 1 by the symbol $\Delta t$.

In practice, the velocity amplitude V is proportional to the applied field strength E, while the time delay $\Delta t$ is independent of field strength. Thus, the ratio V/E, and $\Delta t$ are independent of field strength and depends on particle properties only. The dynamic mobility is defined in terms of these two quantities.

Accordingly, the dynamic mobility of the particle is a complex quantity, denoted by $\mu$, and defined by $$mag\mu = V/E \text{ and } arg\mu = \omega\Delta t$$

where $\omega$ is $2\pi$ times the frequency of the applied voltage in Hertz. The time lag $\Delta t$ increases with particle size, since the particle inertia is proportional to its volume. Thus, the measurement of $arg\mu$ (which depends on $\Delta t$), provides information on particle size, and measurement of $mag\mu$ can then be used to determine particle charge.

This definition of $\mu$ applies to dilute colloids. However, for more concentrated sols, which are likely to be encountered in practice, the above definition must be modified, because the sound waves generated by the electric field can alter the particle motion. The amplitude of this sound wave field will usually be a complicated function of position between the electrodes. Although the applied electric field may be uniform, the particle motion will in general vary with position in a manner which depends on frequency and electrode spacing. If the definition of $\mu$ for dilute colloids was applied in this case, the mobility would also depend on particle position and electrode spacing.

To remove the dependence on particle position, the V in the definition of $\mu$ is taken as the average particle velocity minus the velocity due to the local bulk motion of the suspension. In other words, the velocity that is subtracted out is the component of the particle velocity caused by the bulk motion of the suspension. It is the velocity that the particle would have if the suspension were set in motion by some means other than an applied electric field. By making this modification, the dependence on position and device geometry is removed and a quantity which depends only on particle properties is obtained. A more concise, mathematical definition of the dynamic mobility in concentrated suspensions is set forth in the O'Brien patent application.

THE O'BRIEN METHOD

The O'Brien Method describes how to determine particle size and charge by following a two step process. The first step involves determining the dynamic mobility spectrum by making electroacoustic measurements. The second step involves a calculation procedure to determine size and charge from the dynamic mobility spectrum. As described by O'Brien, there are two types of electroacoustic effects that can be used to determine the dynamic mobility spectrum. One involves applying an unsteady electric field and measuring the resultant acoustic wave and the other involves applying an unsteady mechanical force to the suspension and measuring the resultant electrical response. In general, the preferred operation mode depends on the nature of the material to be measured.

Accordingly, it is desirable to provide an apparatus for determining the dynamic mobility spectrum suitable for use in the first step of the O'Brien Method. The instrument must measure electroacoustic effects over a range of frequencies, i.e., the "electroacoustic spectrum" which is used for obtaining the dynamic mobility spectrum, by applying an unsteady electric field, or an unsteady mechanical force and measuring the electroacoustic effect in either mode.

SUMMARY OF THE INVENTION

Generally speaking, in accordance with the invention, a device for determining the size and charge of colloidal particles by measuring the electrophoretic mobility of the particles by applying an unsteady electric field or unsteady mechanical force of at least two different frequencies and measuring the resultant acoustic wave or electrical response is provided. The device includes a pair of spaced apart acoustic delay elements which may be glass blocks. When the device is used to apply an electric field to excite the particles to generate sound waves, those sound waves are detected by a transducer mounted on the end of one of the glass blocks. When the device is used to apply an unsteady mechanical disturbance to the colloid, the resulting electrical signal is measured by one of the electrodes in contact with the suspension. In either of these two modes of operation, the measured electroacoustic signal depends on the dynamic mobility of the particles and on the acoustic properties of the suspension. To extract the dynamic mobility from these measurements it is therefore necessary to make an independent measurement of those acoustic properties. The second acoustic delay rod is designed to determine these acoustic properties, by measuring the signal from a thin film transducer attached to the end of the rod in contact with the suspension. The electroacoustic signal due to the suspension and the signal from the thin film transducer are fed into a signal processing circuit for determining the Fourier Transforms of these two signals over a range of frequencies.

Accordingly, it is an object of the invention to provide an improved device for determining the electrophoretic mobility of particles in a colloid.

It is another object of the invention to provide a device for measuring the electroacoustic effect of particles in a colloid.

It is a further object of the invention to provide an improved device for applying an unsteady electric field to a suspension and measuring the resulting acoustic effect.

Yet another object of the invention is to provide an improved device for applying an unsteady mechanical disturbance to a suspension and measuring the resulting electrical effect.

It is a further object of this invention to provide an improved device for determining the acoustic properties of the suspension, which are then used in the determination of the dynamic mobility from the electroacoustic signals.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawing(s), in which.

DESCRIPTION OF THE PREFERRED EMBODIMENTS

An instrument designed to measure the dynamic mobility spectrum for suspensions of arbitrary concentration constructed and arranged in accordance with the invention includes two or more metal electrodes energized by a signal generator, with the electrodes in contact with the suspension. The instrument should include a housing for positioning the electrodes apart and maintaining the suspension therebetween. The suspension may be static so long as the particles do not settle during the measurement, or it may be stirred, or flowing in a pipe. In order to determine the dynamic mobility spectrum, the electroacoustic measurements must be made over a range of frequencies which may be achieved in several ways.

In an apparatus for applying an electric field and measuring the resulting acoustic response in accordance with a first embodiment of the invention, a signal generator may be set to generate a single pure sinewave of frequency $f_1$, measure the acoustic result and then be adjusted to another pure frequency $f_2$, and measure the second set of acoustic results and so on for any other frequencies at which the dynamic mobility is to be measured. In accordance with another embodiment, an unsteady electric field may be applied so that the electric field can be made up of several frequencies at once. In still another embodiment, a complex waveform may be applied that has several frequency components (for example, a narrow unipolar voltage pulse approximating a delta function) and then measure the resulting acoustic wave which will be made up of the same frequency components as the applied signal, but with different relative amplitudes and phases.

The signal processing electronics must be able to extract the amplitude and phase of each frequency component of the resulting acoustic or electrical signal in order to construct the dynamic mobility spectrum, as will be described in greater detail below. A key aspect of the instrument design is the ability to excite the suspension with an electric or mechanical field at several frequencies, whether simultaneously or separately. The resulting acoustic or electrical response must then be detected and processed to extract the acoustic or electrical response of the suspension at each pure frequency.

Figure 1:
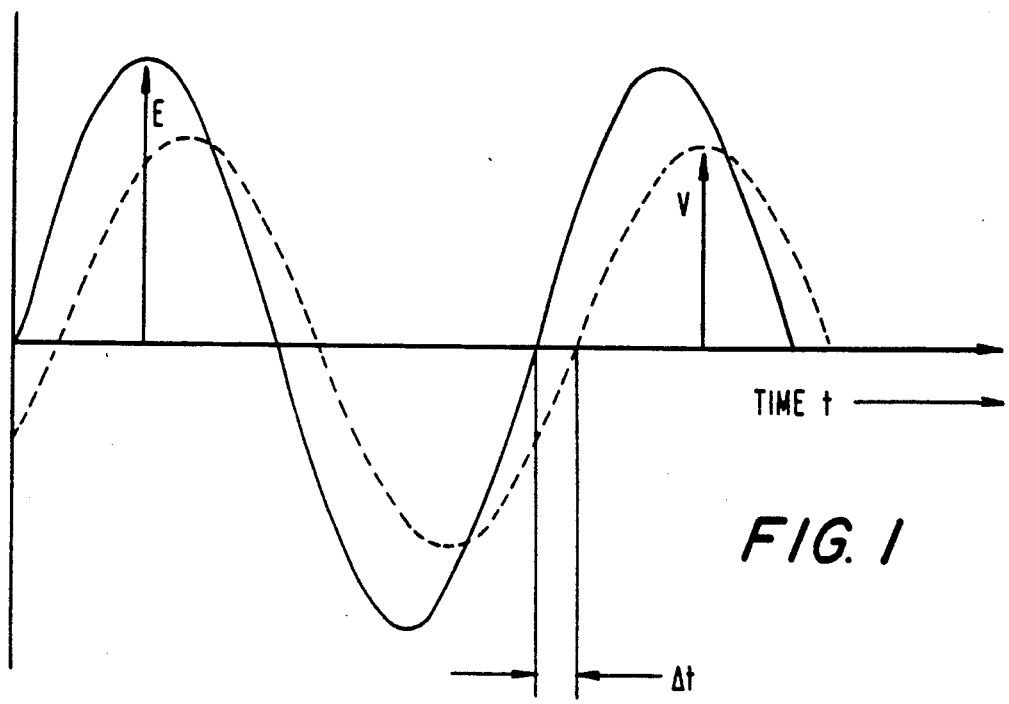
FIG. 1 is a graph showing the electric field strength applied to a suspension and the resulting average particle velocity as a function of time.
Figure 2:
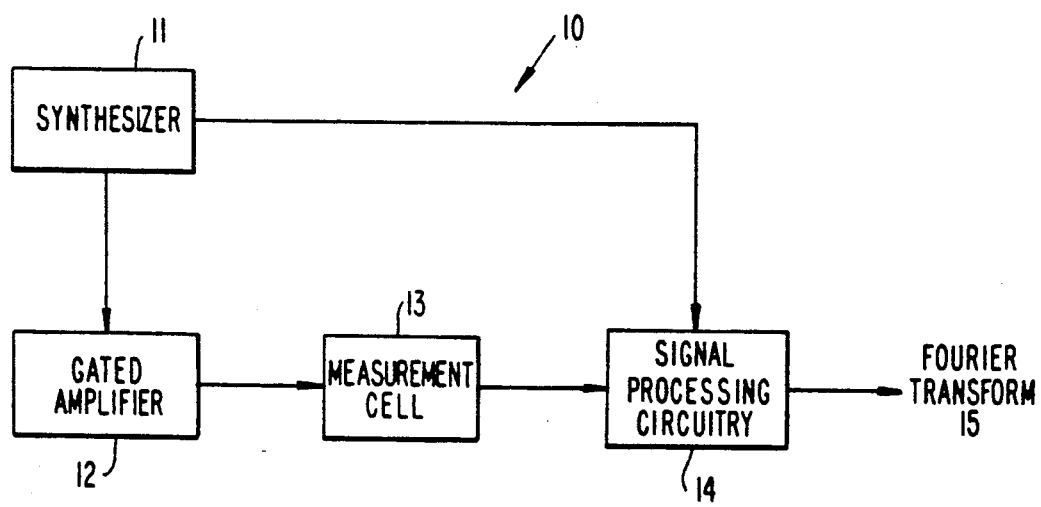
FIG. 2 is a block diagram showing the main components of a device for measuring the dynamic mobility spectrum for suspensions of arbitrary concentration constructed and arranged in accordance with the invention.

The block diagram of an instrument for applying an electrical field and measuring the acoustic wave generated is shown in FIG. 2. The instrument includes four main components: a synthesizer 11 for producing a continuous sinusoidal voltage over a broad range of frequencies; a gated amplifier 12 which produces a pulse of sinusoidal voltage coherent with the continuous wave; a cell 13 which contains a suspension to be measured and produces output voltage signals in response to the applied pulses, and a signal processing circuit 14 for generating Fourier Transforms 15 of the signals from cell 13. The design and functions of cell 13 and the signal processing scheme are described below in greater detail.

Figure 3:
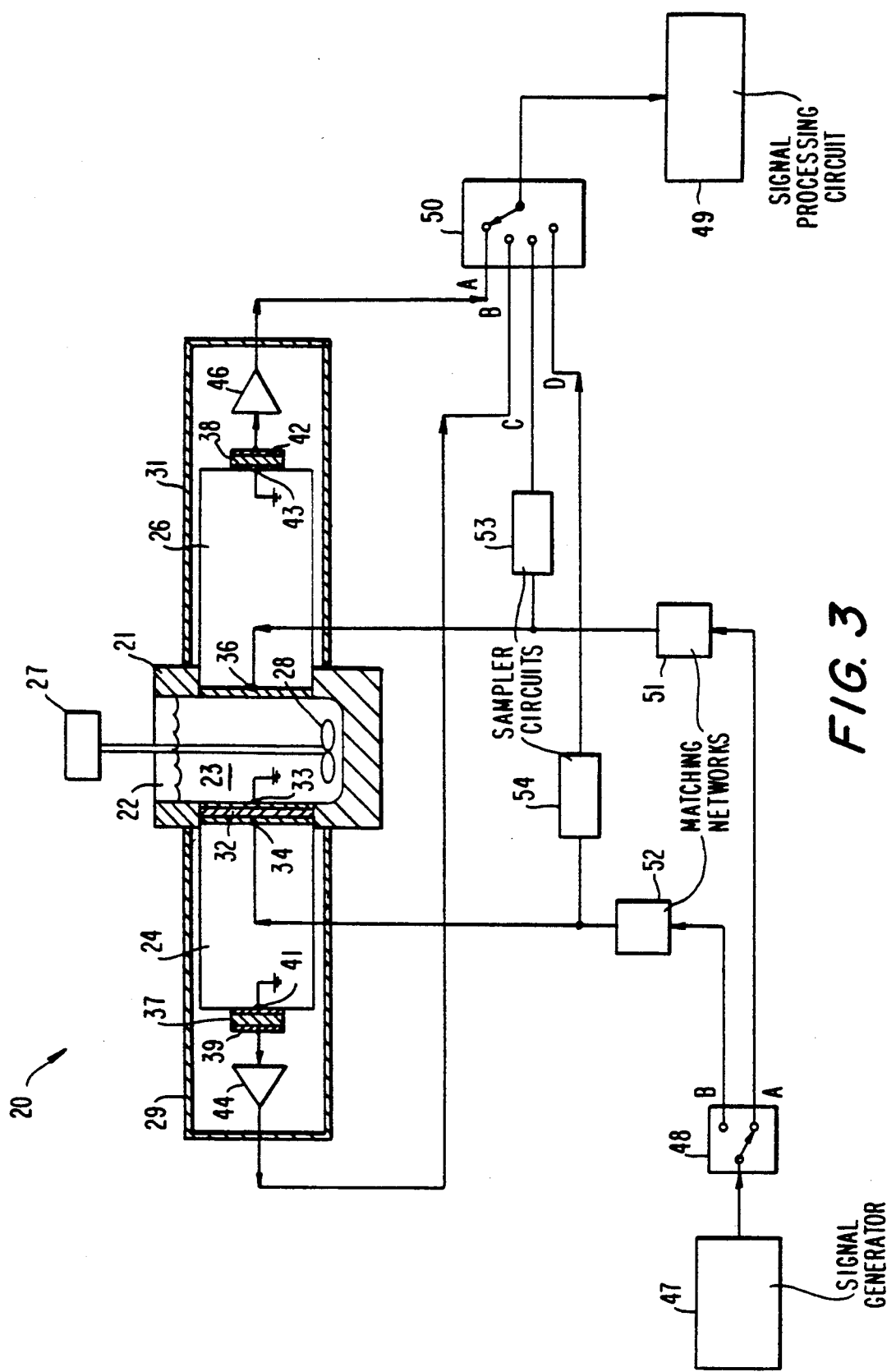
FIG. 3 is a cross-sectional view in schematic of an instrument for applying an unsteady electric field to a suspension and measuring the acoustic response in accordance with a first embodiment of the invention.

Referring now to FIG. 3, an instrument 20 (i.e., a sensor) for measuring the electroacoustic effects constructed and arranged in accordance with a first embodiment of the invention is shown. Sensor 20 includes a suspension housing 21 with a cavity 22 of a suitable plastic material for holding a suspension 23 to be measured. Suspension 23 is held in cavity 22 between and in contact with electrodes for applying the electric field.

Sensor 20 includes a first acoustic delay rod 24 and a second acoustic delay rod 26 mounted on opposing sides of housing 21 in contact with suspension 23. In the illustrated embodiment, cavity 22 is a 2.5"×2.5"×4.5" container. A mixer 27 having a paddle type stirrer 28 is centered in cavity 22 to prevent particles in suspension 23 from settling. Additional sensors for measuring the temperature, pH and conductivity of the suspension along with a heat exchanger for temperature control, may be inserted from above into suspension 23, but are not shown in FIG. 3.

Sensor 20 includes a first side chamber 29 for mounting first delay rod 24 a second side chamber 31 for mounting second delay rod 26. Side chambers 29 and 31 are bonded to suspension housing 21. A 1.5" diameter aperture exposes delay rods 24 and 26 to suspension 23 in cavity 22. A thin piezoelectric transducer 32 is mounted on the face of first delay rod 24 exposed to suspension 23. A gold electrode 33, which is grounded, is disposed on the outside of transducer 32 wetted by the suspension. A second transducer electrode 34 is disposed on delay rod 24 and the inside surface of transducer 32. Electrode 34 and grounded electrode 33 form an electrode pair for applying an electric field across transducer 32.

A single gold electrode 36 is disposed on the face of second delay rod 26 in contact with suspension 23. Electrode 36 and grounded transducer applying electrode 33 form an electrode pair for applying an electric field across suspension 23. These electrodes are plane parallel and separated by distance of approximately 2.5". It is desirable to have the electrodes parallel to each other with a separation distance comparable or smaller than their diameter so that the electric field distribution across the electrodes is fairly uniform.

Each delay rod 24 and 26 has a first and a second receiving transducer 37 and 38, respectively mounted on the end opposite suspension 23. First receiving transducer 37 is a piezoelectric transducer and has a gold electrode 39 mounted on the end away from cavity 22 and a gold electrode 41 mounted between first delay rod 24 and transducer 37 which is grounded. Similarly, second receiving transducer 38 has an external gold electrode 42 and a grounded gold electrode 43 between transducer 38 and a second delay rod 26. Transducers 38 is used to detect the acoustic waves generated by the particles in suspension 23 in response to the electric field across suspension 23. Transducer 37 is used to detect the acoustic wave generated by the thin film transducer 32 in response to the electric field across transducer 32. A first preamplifier 44 and a second preamplifier 46 are mounted in side chambers 29 and 31, respectively. Each receiving transducer 37 and 38 is connected to a preamplifier for amplifying the signals generated by receiving transducers 37 and 38 before they are fed for signal processing.

Figure 4A:
FIG. 4A is a waveform illustrating the output waveform typical of the synthesizer in the device of FIG. 2.
Figure 4B:
FIG. 4B is a waveform showing the modulation pulse for turning the gated amplifier signal generator on in the device of FIG. 2.
Figure 4C:
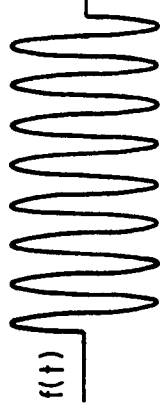
FIG. 4C is a waveform illustrating the gated sinusoids generated by the gated amplifier signal generator in the device of FIG. 2.

A signal generator 47 known as a "gated amplifier" for producing pulses which are gated sinusoids as shown in FIG. 4C is connected to applying transducer electrode 34 and electrode 36 for applying the electric field across suspension 23. A frequency synthesizer produces a pure frequency continuous sinewave voltage which is applied to gated amplifier 47. A modulation pulse, phase coherent with the sinewave, turns on gated amplifier 47 for the duration of a modulation pulse shown in FIG. 4B causing the gated amplifier to amplify the sinewave signal into a large amplitude (in the order of 200 volts) as shown in FIG. 4C. This pulse is applied either across suspension 23, via matching network 51, or across thin film transducer 32, via matching network 52 selectively by a switch 48.

A sensor constructed and arranged in accordance with the invention includes a circuit element 53 for sampling the pulse applied to the suspension electrodes and an identical circuit element 54 for sampling the pulse applied to the thin film transducer electrodes. This circuitry is necessary because the amplitude and phase of the signal applied to the sensor components must be known with a high degree of accuracy. At the frequencies used in this instrument, parasitic circuit elements require that measurements be made as close to the actual electrode contacts as possible to minimize errors. The sampled signals are measured when the four-way switch 50 is in positions C and D as shown in FIG. 3. When the switch 50 is in position C the voltage across the suspension is sampled and fed to the signal processing circuit 49. When the switch 50 is in position D the voltage across the thin film transducer 32 is sampled and fed to signal processing circuitry 49.

Delay rods 24 and 26 are formed of glass blocks to provide an acoustic delay, because they exhibit very low acoustic loss in a frequency range 0.25 to 20 MHz and can be very closely matched. Matching between the acoustic delay lines is important since the processing of the signals requires that the signal paths seen by the suspension signal and the thin film transducer signal be identical. In this manner, the amplitude changes and the phase shifts in the instrument cancel when one signal is referenced to the other. Accordingly, this configuration allows for accurate measurements of very small phase shifts without sensitivity to parasitic circuit elements in the electronics and device temperature coefficients. Another important design element is the shape and size of the delay rods 24 and 26. By using rectangular cross sections for the glass as opposed to circular or square cross-sections, spurious acoustic wave modes can be eliminated which typically interfere with the desired signals.

The glass blocks forming delay rods 24 and 26 used in sensor 20 serve several purposes. The glass blocks provide an acoustic delay that separates the received signal in time from the high level applied electric field signal. It takes several tens of microseconds for the acoustic wave generated at electrode 34 and 36 to travel down the 5" length of glass blocks 24 and 26 and strike receiving transducer 37 and 38. The duration of the applied sinusoidal pulse is chosen such that it is turned off by the time the signal arrives at receiving transducer 37 and 38. This eliminates any problems with cross-talk interference between the high level applied electric field pulse and the very low level signals generated at receiving transducer 37 and 38. Therefore, in the design, the glass block length, pulse duration, and electrode separation distance are optimized to prevent cross-talk.

According to O'Brien's electroacoustic theory, O'Brien, R. W. 1988 "Electroacoustic Effects In A Dilute Suspension Of Spherical Particles" *J. Fluid Mech.* 190, 71, the sound waves emitted by the particles in an applied electric field manifest themselves at the electrode boundaries, making it appear that the soundwaves are coming from the electrodes. Some of this acoustic energy travels down delay rods 24 and 26 and some travels out into suspension 23. If the electric field remains on long enough, vibrations from one electrode will travel across suspension 23 and reach the opposite electrode causing an interference between the two signals. In this case, the electrode to electrode distance must be adjusted so that the two signals constructively interfere setting up a standing wave between the two electrodes. This is a difficult condition to meet in practice when one has to operate at several different frequencies. To avoid this problem, the electric field is turned off before the vibrations from one electrode reach the other as will be explained in greater detail below.

In addition, the field strengths required for measuring the electroacoustic effects can generate large currents in the suspension if the ionic conductivity is very high. This can lead to significant heating of the suspension if the field is applied continuously. By using short pulses with low repetition rates (duty cycle typically 1%) any problems associates with electrical heating can be eliminated.

Receiving transducers 37 and 38 which detect the generated acoustic signals, are formed with a piezoelectric crystal material bonded to the ends of delay rods 24 and 26 to detect the amplitude and phase of the sound waves launched down delay rods 24 and 26. An important requirement of receiving transducers 37 and 38 is that they be capable of detecting the sound waves over the frequency range required to determine particle size and charge. This is a classic design problem encountered quite often in acoustics.

In an exemplary embodiment, a crystalline piezoelectric material, such as lithium niobate is used. This crystal is able to respond over a wide frequency range by operating at overtone frequencies of the fundamental resonant frequency of the crystal. Transducers of this type have a fundamental resonant frequency that corresponds to the frequency where the crystal is one half wavelength thick. The equation for this condition referred to as the fundamental resonant frequency is approximately given by:

$$F_r = \frac{\text{velocity of sound for the crystal}}{2 \times \text{Crystal Thickness}}$$

The crystal will also resonate at frequencies corresponding to odd multiples of the fundamental resonant frequency (i.e., $3F_r, 5F_r, 7F_r, \ldots NF_r$). In addition, it is possible to operate the transducer at frequencies below its fundamental frequency with some loss in sensitivity. In an exemplary embodiment, transducers with a fundamental resonant frequency of 0.5 MHz are utilized which can achieve an overall frequency range of 0.25 to 20 MHz (or higher). In this configuration, sensor 20 can operate at discrete frequencies above 0.5 MHz corresponding to the overtone frequencies of the crystal.

In another embodiment, a "broadband piezoelectric transducer" may be utilized which operates at frequencies below its fundamental frequency. The drawback with this design is that there is a significant loss in sensitivity. There are even optical detection devices where a laser beam could be scanned across the surface of the glass and the sound waves detected by interferometry. To obtain a working device, the device must be provided with means for measuring both the amplitude and phase of the sound waves over the optimal sizing frequency range. The O'Brien method provides criteria for the optimal sizing frequency range which depends on the particle size range over which the instrument must operate.

The sound waves generated in delay rod 26 by the application of the electric field across the suspension depend on the dynamic mobility and the acoustic properties of the suspension 23. The more concentrated suspension 23, the more the acoustic properties will differ from those of the pure solvent. In order to determine accurately the dynamic mobility spectrum for arbitrary particle concentrations, sensor 20 must have an accurate way to account for how the particle concentration affects the measured signal at the other end of a delay rod. This result is achieved by bonding thin piezoelectric film 32 on the surface of one delay rod 24. When the electric field is applied across electrode pair 33 and 34, the transducer expands and contracts at the applied frequency, generating sound waves in the adjoining delay rod 24 and in suspension 23. This sound wave field depends on the acoustic properties of the suspension 23. When the sound waves in delay line 24 reach transducer 37 they generate a voltage across electrode pair 39 and 41. The acoustic properties of the suspension are determined from the measurement of this signal.

The O'Brien Method provides a formula that shows how to normalize out the suspension concentration effect by taking the ratio of the electroacoustic signal to that of the signal from thin film transducer 32. This procedure is slightly more complicated when operated at frequencies so high that the thickness of the thin film transducer is no longer small relative to the acoustic wavelength. In an exemplary embodiment, polyvinylidene fluoride (PVDF, a piezoelectric polymer) or a copolymer of PVDF is utilized. However, sputtered films of crystalline zinc oxide or any other thin film piezoelectric materials may also be used.

Thin film transducer 32 on first delay rod 24 provides another very useful function. Since delay rods 24 and 26 are matched, the thin film transducer signal and the suspension electroacoustic signal have identical signal processing paths. Therefore, the ratio of the two signals in essence divides out any variation in the phase and amplitude of the signals due to drift in the electronics or thermal expansion effects in delay rods 24 and 26. Accordingly, a very high level of stability and reproducibility for sensor 20 is achieved.

There are other approaches to account for the effect of the suspension acoustic properties on the electroacoustic signal. For example, it is possible to measure the suspension acoustic impedance by using a reflectance measurement. In this method, a sound pulse is launched down a glass block and is partially reflected at the delay rod (i.e., suspension interface). The ratio of the reflected signal to the incident acoustic wave is defined as the reflection coefficient. The reflection coefficient depends on the delay rod/suspension acoustic impedance ratio and can be used to calculate the acoustic impedance of the suspension. This method is not nearly as sensitive as the use of the thin film transducer described above, but may prove useful for abrasive suspension environments which would quickly destroy a fragile thin film transducer (i.e., on-line measurements in slurry pipelines).

A detailed discussion of the operation of sensor 20 of FIG. 3 is set forth below. When computer-controlled switch 48 is set in a first position A, the voltage pulse from gated amplifier signal generator 47 is applied across transducer electrode 36. This voltage pulse, as shown in FIG. 4C, causes the particles in suspension 23 to accelerate backwards and forwards, thereby generating sound waves. More specifically, some form of pulse source is required for energizing the suspension electrodes and the thin film transducer. The pulse may be a gated sinusoid or some other type of time varying voltage. The pulse source must be capable of generating pulses with frequency components that span the frequency range required for sizing the particles. The pulse waveform must be reproducible for repetitive measurements or a separate means for monitoring the pulse waveform must be provided.

In an exemplary embodiment, sensor 20 uses gated sinusoids with a carrier frequency determined by the frequency of the continuous sine wave fed to the gated amplifier. A gated sinusoid contains frequency components other than the carrier frequency it was generated from. In fact, all pulsed waveforms will in general contain more than one frequency component. The subsequent signal processing circuit must be capable of extracting the phase and amplitude of the various frequency components of the signal. Sensor 20 steps through a number of frequencies (approx. 15-20) by varying the frequency of the gated amplifier carrier so that sensor 20 operates at the resonant frequencies of the lithium niobate receiving transducers.

The O'Brien Method discloses that the macroscopic sound waves in such a device appear to emanate from the electrodes, even though the waves are in fact generated by the particles. Thus, the applied voltage pulse causes sound waves to propagate out from the front and back of each electrode in suspension 23 and along adjoining delay rods 24 and 26. When the sound wave pulse reaches the end of second delay rod 26, the sound wave excites a voltage $S_1(t)$ in second receiving transducer 38. This voltage is amplified by preamplifier 46 and fed into signal processing circuit 48 through a switch 50.

Figure 5:
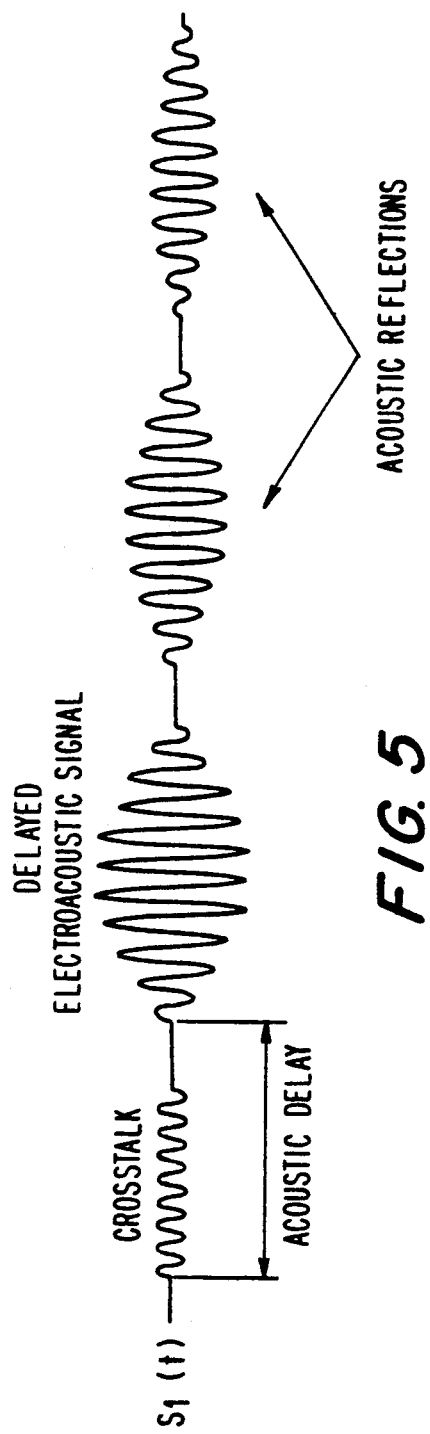
FIG. 5 is a typical oscilloscope trace of the amplified signals from the receiving transducers in the device of FIG. 3 which measure the acoustic response in the suspension.

A typical oscilloscope trace of this signal is shown in FIG. 5. The first wave form on the trace occurs as the electric field is being applied across the cell. This waveform has nothing to do with sound waves, but rather is caused by "cross-talk" which is unwanted electromagnetic radiation from the applied pulse. In order to avoid this signal, pulses and delay rods are provided. In this manner, by the time the sound wave has reached the transducer at the end of the delay rod, the applied pulse has been turned off.

The second waveform in FIG. 5 is caused by the sound wave striking second receiving transducer 38. This signal clearly depends on the dynamic mobility of the particles, since it is generated by the motion of the colloidal particles in the applied field. However, the signal also depends on the acoustic properties of suspension 23 and delay rod 26. In order to extract the dynamic mobility from the measured signal, it is necessary to have an independent measurement of these quantities.

The measurement of these properties is performed by first delay rod 24. As previously described, first delay rod 24 is identical to delay rod 26, except that thin film transducer 32 bonded to the face in contact with suspension 23. Transducer 32 is made of a film of material such as zinc oxide or polyvinylidene fluoride, sandwiched between two very thin layers of gold 33 and 34. Gold metal layer 33 in contact with suspension 23 forms the second electrode in suspension 23 for applying the electric field across suspension 23. Transducer 32 expands when a voltage of a first polarity is applied across the film, and contracts when a voltage of opposite polarity is applied.

When switch 48 is moved to position B, the voltage pulse is applied across transducer 32 causing it to expand and contract alternately. This motion generates sound waves which propagate into suspension 23 and along first delay rod 24. The sound wave pulse excites a voltage in first receiving transducer 37 which is then fed to first preamplifier 44 and into signal processing circuit 49. This signal depends on the acoustic properties of suspension 23 and is used to determine those properties. By combining the voltage signal from first receiving transducer 37 and the signal from second receiving transducer 38, the dynamic mobility is obtained. The steps involved in the determination of $\mu$ from these signals will be described below.

In order to avoid the complications caused by multiple reflections, the duration of the voltage pulse is set so that the pulse is turned off by the time the sound waves have travelled across cavity 22. Thus, when the switch is in position A, the first pulse after the cross talk in the waveform in FIG. 5 is due to the electroacoustic signal from the second electrode 36. Subsequent pulses are caused by reflections of the sound waves at the ends of each delay rod 24 and 26. With switch 48 in position B, the first pulse after the cross-talk results from the sound field of thin film transducer 32. There is no signal produced by electrode 36 in this case. Therefore, all subsequent pulses are reflections of that transducer signal from transducer 32.

Figure 6:
FIG. 6 is a waveform showing a gated signal after cross-talk and unwanted acoustic reflections are stripped away.

In signal processing circuit 49, the signal is "gated", so that all the signals, except the first pulse after the cross talk is stripped away. This gated signal, which we will denote by f(t), is illustrated in FIG. 6.

Figure 7:
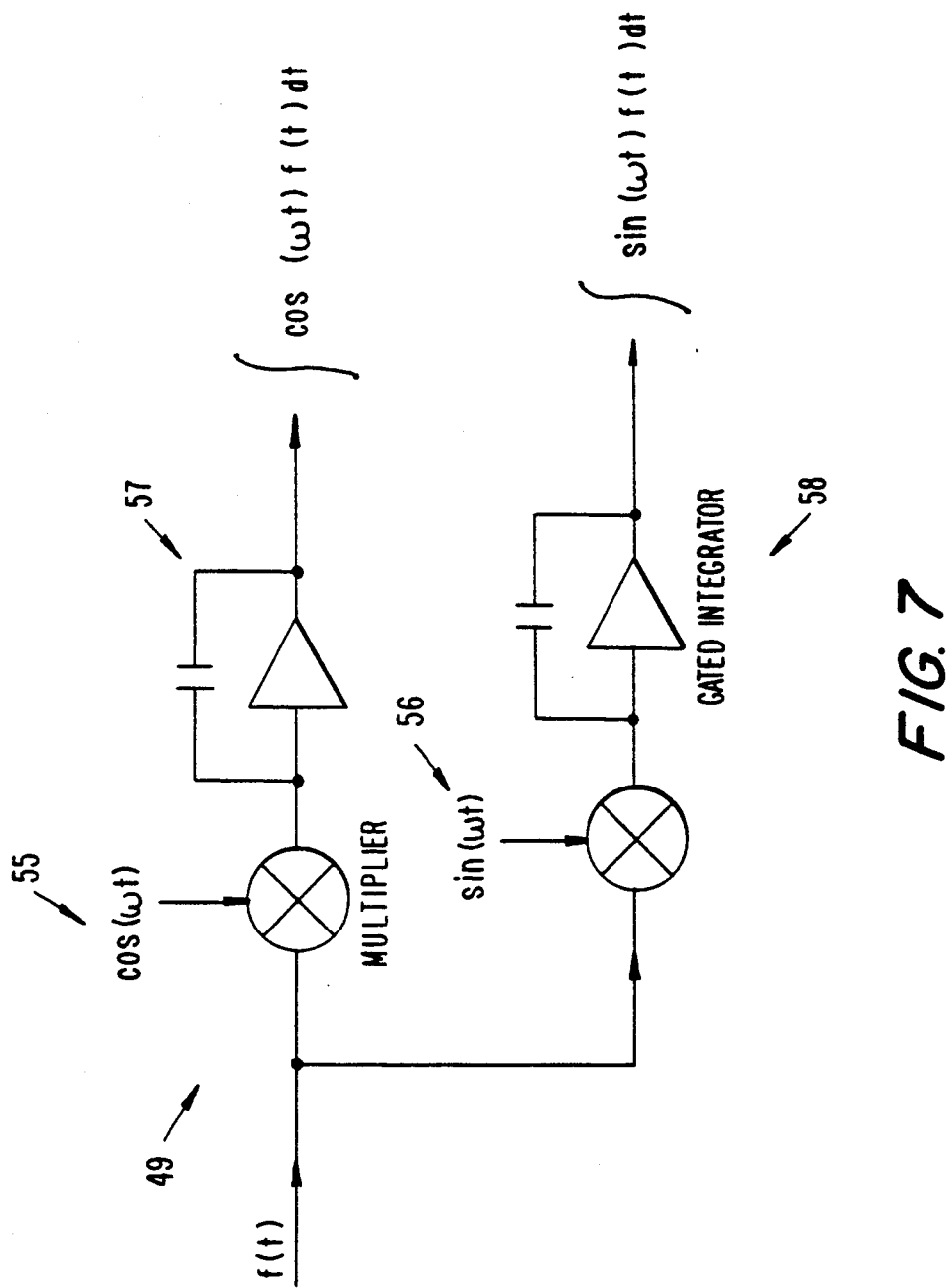
FIG. 7 is a schematic illustration of the signal processing circuit of the sensor of FIG. 3.

A simplification of signal processing circuit 4 is shown in FIG. 7. The path carrying the signal divides into two branches. In a first path, the signal is multiplied by cos ($\omega$t) by a multiplier 55 and in a second path by sin ($\omega$t) by a multiplier 56. These sinusoidal signals are generated by the same source that feeds the sin($\omega$t) input to a gated amplifier in signal generator 47. Gated amplifier in signal generator 47 is designed to produce a pulse which is coherent with the input and which turns on as the input swings from a negative to positive voltage. In this way, gated amplifier 47 generates a reproducible pulse, phase locked to the "reference" voltage sin($\omega$t).

After the multiplication stage, the two signals are fed to a pair of gated integrators 57 and 58, respectively. These circuits integrate the gated pulse, and sample and hold circuits output DC voltages proportional to the integrals of f(t)cos($\omega$t) and f(t)sin($\omega$t) over the duration of the pulse.

These two signals pass, through an analog/digital converter board, to a computer where the signals are stored as the single complex number F($\omega$) defined by $$F(\omega) = \int (\cos(\omega t) + i\sin(\omega t))f(t)dt$$
$$= \int e^{i\omega t} f(t) dt$$

Such integrals are referred to in the mathematical literature as the "Fourier Transform" of f(t). As indicated by the formula, the value of F depends on the transform frequency. The low level signals from the receiving transducers must be amplified and then processed to produce the Fourier Transform of the signal at the frequency of the gated amplifier carrier.

In order to determine the phase shift and amplitude, the Fourier Transform is utilized since it extracts the desired frequency component in the presence of other frequency components created by transients or distortion of the signals. However, there are many ways to determine the Fourier Transform of the signals. In an alternative embodiment, the amplified receiving transducer signal is simply digitized using a very high speed analog to digital converter and then the Fourier Transform is calculated from the digitized data.

In summary, at each frequency, the device produces two signals: one generated by the pulse applied to suspension 23 and the other by the pulse applied to thin film transducer 32. Signal processing circuit 49 converts each of these signals into a complex number, representing the Fourier Transform of the gated signal at the frequency of the applied pulse. The device is designed to operate over a range of frequencies and thus, produces a spectrum of Fourier Transforms. It is from this spectrum that the dynamic mobility spectrum referred to in the O'Brien Method is determined.

In order to explain how the dynamic mobility is extracted from the Fourier Transform, let $f_1(t)$ denote the gated version of the signal generated by the electric field on the suspension and $F_1(\omega)$ denotes the Fourier Transform of $f_1(t)$. This transform should depend on the dynamic mobility $\mu(\omega)$, since the signal is generated by the particle motion in an electric field.

In order to determine the link between $F_1(\omega)$ and the dynamic mobility it is necessary to draw on theoretical results obtained in O'Brien's electroacoustic papers, O'Brien, R. W. 1988, "Electroacoustic Effects In A Dilute Suspension Of Spherical Particles", *J. Fluid Mech.* 190, 71 and O'Brien, R. W. 1990, "The Electroacoustic Equations For A Colloidal Suspension" *J. Fluid Mech.* 212, 81. In these studies, the applied electric field is taken to be a pure sinusoid, rather than the pulsed sinusoid used in the exemplary device. However, it can be shown that in a linear system, the Fourier Transform of the output, which is a quantifiable measurement, can be calculated by taking the applied voltage to be a sinusoid at the transform frequency $\omega$. To be more precise, the transform is obtained by calculating the output for a complex input voltage of the form $V_o e^{-i\omega t}$. Thus, O'Brien's analysis can be readily applied to the device described herein. In fact, signal processing circuit 49 was designed to determine the Fourier Transform.

Application of the O'Brien analysis to sensor 20 is simplified by the fact that signal processing circuit 49 determines the Fourier Transform of the signal emanating from the electrode on one of the delay rods, with all echoes stripped away. Thus, in calculating the Fourier Transform of these signals, the presence of the opposing rod is neglected, since it has no effect on the measured signal. Therefore, the sound waves can be calculated as if they were radiating into an infinite volume of suspension.

When a sinusoidal electric field acts on suspension 23, the particles near the electrodes move alternating towards and away from the electrode. As the particles move, they drive a back flow of liquid in the opposite direction. O'Brien, R. W. 1988, "Electroacoustic Effects In A Dilute Suspension Of Spherical Particles", *J. Fluid Mech.* 190, 71 and O'Brien, R. W. 1990, "The Electroacoustic Equations For A Colloidal Suspension" *J. Fluid Mech.* 212, 81 has shown that these opposing particle and liquid motions at the electrodes result in an alternating flux of momentum. Thus, the electric field drives a flow at the electrodes. As a result, the suspension velocity (the momentum per unit mass) at the electrode is different from the electrode velocity. O'Brien, R. W. 1988, "Electroacoustic Effects In A Dilute Suspension Of Spherical Particles", *J. Fluid Mech.* 190, 71 and O'Brien, R. W. 1990, "The Electroacoustic Equations For A Colloidal Suspension" *J.*

*Fluid Mech.* 212, 81 shows that this "jump" in velocity between the electrode and the suspension is given by:

$$\phi \frac{\Delta \rho}{\rho} \mu E$$

wherein $\phi$ is the fraction of the suspension volume taken up by particles, $\rho$ is the solvent density and $(\rho+\Delta\rho)$ is the particle density; and E is the electric field at the electrode. From a mathematical point of view, it is this jump in velocity at the electrodes that drives the sound waves. Therefore, the sound waves appear to emanate from the electrodes.

The sound waves generated by this velocity jump will be proportional, in amplitude, to the quantity $\phi(\Delta\rho/\rho)\mu E$. Unfortunately, the constant of proportionality depends on the acoustic properties of the suspension, which are unlikely to be known apriori.

As set forth above, the dependence on acoustic properties is accounted for by using thin-film transducer 32. In order to describe this dependence, let $F_2(\omega)$ denote the Fourier Transform of the gated version of the signal generated by the electric field on the thin film transducer 32. The thickness of the transducer is assumed to be much less than the sound wavelength. At present, the thinnest available films are a few microns thick. Therefore, this assumption limits the analysis to frequencies of less than 10 MHz, where the sound wavelength is around 0.2 mm. The analysis for higher frequencies will be discussed below.

In this thin film limit, the applied voltage causes transducer 32 to expand and contract independent of the acoustic properties of delay rod 24 or suspension 23. Thus, the opposing faces of transducer 32 move with different velocities. Therefore, there is a jump in velocity across transducer 32, and that jump is independent of the acoustic properties of suspension 23. Hence, transducer 32 mimics the action of the electric field on suspension 23 by causing a velocity jump between suspension 23 and the face of delay rod 24. Thus, the acoustic signal generated in delay rod 24 by thin-film transducer 32 depends on the acoustic properties of suspension 23 in the same way as the electroacoustic signal in delay rod 26.

By taking the ratio of the signals, $F_1(\omega)/F_2(\omega)$, a value is obtained which is independent of the acoustic properties of suspension 23 and which is proportional to $\phi(\Delta\rho/\rho)\mu$. The constant of proportionality depends on properties of thin-film transducer 32 and on the distribution of the electric field over the electrode. If the amplitude of the applied pulse is held fixed and if the complex conductivity of suspension 23 is much greater than that of the walls of the container 21 (as is usually the case for aqueous sols in a dielectric container), the field distribution will be independent of suspension properties. Thus, the constant of proportionality linking $F_1/F_2$ to $\phi(\Delta\rho/\rho)\mu$ is a device constant which can be determined at each frequency from measurements of $F_1/F_2$ for a suspension with a known dynamic mobility spectrum.

By calculating the ratio $F_1/F_2$, the dependence on the acoustic impedance of the suspension is not only eliminated, but any variations in the individual signals due to effects such as thermal expansion of the delay rods 24 or 26 or drifts in signal processing circuit 49 is also eliminated. This occurs due to the fact that both signals pass down identical delay rods and through signal processing circuit 49. Thus, these variations divide out when calculating the ratio.

The above technique tends to break down at high frequencies, when the sound wavelength is not large compared to the transducer thickness. In this case, the velocity jump across the transducer depends on the acoustic properties of the suspension. Therefore, the ratio $F_1/F_2$ also depends on the acoustic properties of the suspension. A different approach is used which makes use of the fact that the wavelength is now much smaller than the dimensions of the electrodes.

In this limit, the sound waves field in the neighborhood of the electrode are approximately planar, and the wave field in that region can be calculated using the assumption that the pressure and velocity only depend on the distance from the electrode. That is, the sound wave field is locally the same as that generated by an infinite flat electrode. In the calculation of the electroacoustic wave, the motion is driven by a spatially uniform electric field normal to the electrode. The solution of the equations for the velocity and pressure in this case is straightforward. From that solution, it is determined that $F_1$ is given by:

$$F_1 = A\phi \frac{\Delta\rho}{\rho} \mu \frac{Z_s}{Z_r Z_s} \quad [1]$$

wherein $Z_r$ is the "acoustic impedance" of the delay rod (equal to density times the speed of sound), and $Z_s$ is the acoustic impedance of the suspension. The quantity A in this expression is independent of the suspension properties; it is a device factor. The acoustic impedance of the delay rod can be readily determined. The signal from the thin film transducer 32 can be written in the form $$F_2 = \alpha + \frac{\beta Z_s}{Z_r' + Z_s} \quad [2]$$

wherein $\alpha$, $\beta$ and $Z_r'$ are device parameters, independent of the suspension. $Z'_r$ is the acoustic impedance of the delay rod/transducer film combination; that is the acoustic impedance "seen" from the suspension. The three parameters $\alpha$, $\beta$ and $Z_r'$ can be determined from the measurements of $F_2$ with three fluids of known acoustic impedances. In the exemplary embodiment, air, water and n-heptane are used as the three fluids. Once these parameters have been determined, $Z_s$ can be determined by measuring $F_2$ for the suspension and using the above equation. If 100 and $\Delta\rho/\rho$ are known for the suspension, $\mu$ can then be obtained from $F_1$ with the aid of equation [1] above.

Accordingly, the two procedures set forth above for determining $\mu$ cover all possible frequencies. Thus, the instruments described herein enable using the O'Brien Method for the determination of the dynamic mobility in a suspension of arbitrary concentration.

This technique for determining acoustic properties by the use of a thin film transducer is one of a number of possible techniques for determining acoustic properties. In another embodiment, the acoustic properties could be determined by applying the voltage pulse to transducer 38. This would generate a sound wave which would travel down rod 26. When the sound wave reaches suspension 23, a fraction of the wave energy will be reflected back down rod 26. The amplitude of the reflected wave depends on the acoustic properties of the suspension. Thus, when the reflected wave reaches transducer 38 it generates a signal which can be used for determining the acoustic properties of the suspension. Thus, the acoustic properties can be determined by applying a voltage pulse to transducer 38 and measuring the voltage pulse generated across that transducer by the reflected wave. This method is not as accurate as the method involving the thin film transducer, but it could prove advantageous in applications involving corrosive suspensions which could damage a thin film transducer.

Figure 8:
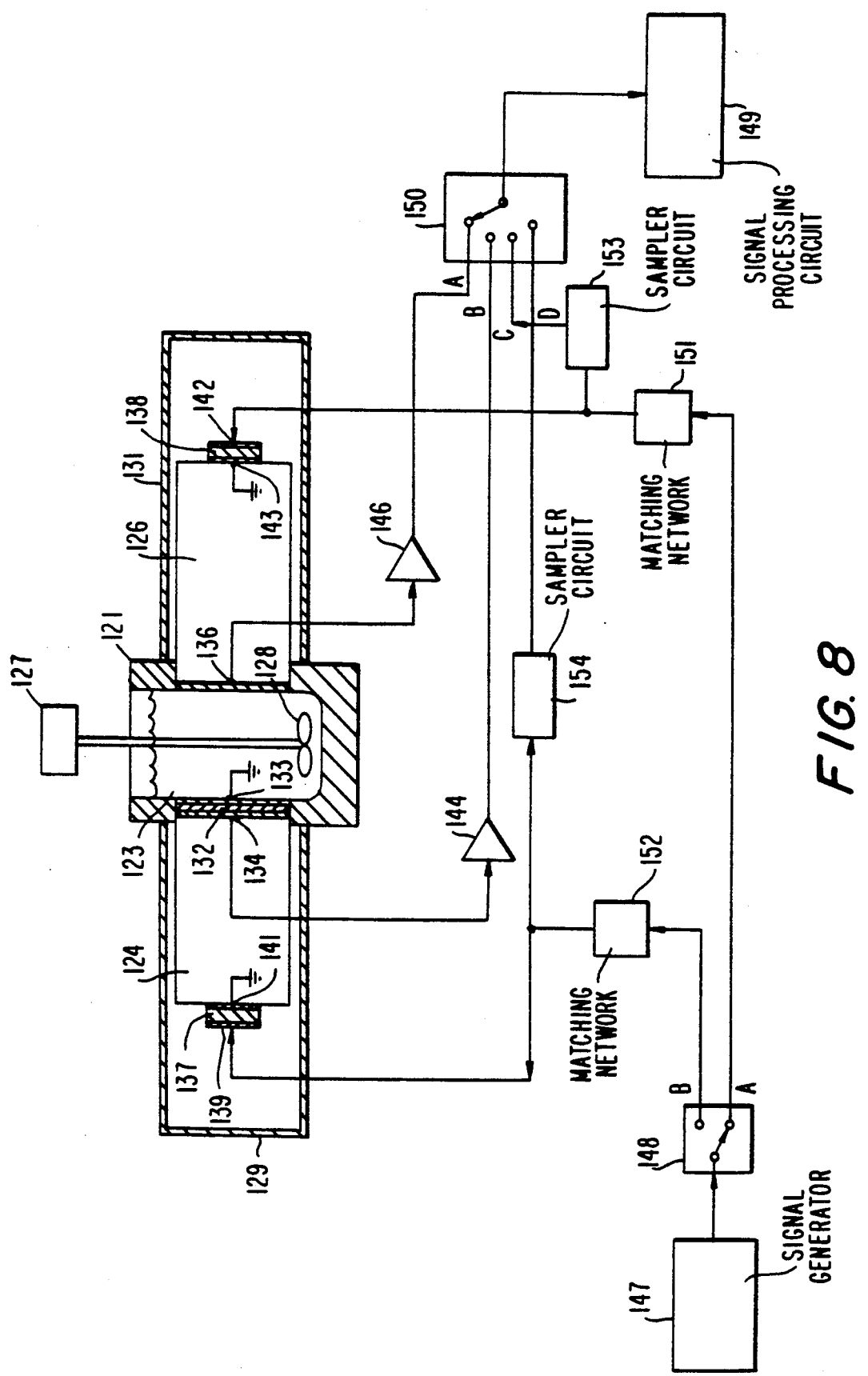
FIG. 8 is a cross-section in schematic of an instrument for applying an unsteady mechanical field to a suspension and measuring the resultant electrical response in accordance with another embodiment of the invention.

As described by O'Brien, there are two types of electroacoustic effects that can be used to determine the dynamic mobility spectrum, one involving the generation of sound waves by the application of an unsteady electric field to the suspension, and the other involving the generation of voltages and electric currents across the suspension by the application of an unsteady mechanical disturbance. Sensor 20 for measuring the first type of electroacoustic effect has been described in detail. Sensor 20 can also be used to obtain mobility spectra from measurements of the second type of electroacoustic effect by slight modification as shown in the schematic of FIG. 8 of a sensor 120. All similar elements of sensor 20 in FIG. 3 which are present in sensor 120 of FIG. 8 have the same reference numeral preceded by the digit "1".

To operate the sensor 120 in this second mode, it is necessary to change the input and output connections to cell 113 as shown in FIG. 8. The input voltage passes through a switch 148 which directs the signal to either one of a pair of transducers 137 and 138 at end of corresponding rods 124 and 126. When switch 148 is in the A position, the signal is directed to transducer 138, and when switch 148 is in the B position, the signal is directed to transducer 137. The applied voltage causes transducer 137 to expand and contract, thereby generating sound waves. When the input voltage is applied to transducer 138, the resulting sound waves pass down rod 126 and into suspension 123. As the waves pass into suspension 123 an electroacoustic effect of the second type is generated, resulting in an electrical signal at electrode 136.

Let $F_1$ denote the Fourier Transform of this signal at electrode 136. According to the O'Brien Method, $F_1$ is proportional to the dynamic mobility of the particles and proportional to the intensity of the sound wave pressure at the electrode. This sound wave pressure depends on the acoustic properties of suspension. As discussed above, these properties depend on particle concentration and are not usually known apriori. To determine the dynamic mobility it is therefore necessary to measure the sound wave pressure independently. This is done by switching the applied voltage pulse to transducer 137. The resulting sound wave passes down rod 124 and into suspension 123. As it passes through thin film transducer 132 a voltage pulse is generated at electrode 134.

Let $F_2$ denote the Fourier Transform of this signal at electrode 134. This quantity is proportional to the intensity of the pressure of the sound wave acting on electrode 133. Since transducers 137 and 138 and rods 124 and 126 are identical, the sound waves in both rods will be the same. Provided that transducer 132 is so thin that it does not impede the sound wave, the pressure at electrode 133 will be the same as the pressure acting on electrode 136 during the measurement of $F_1$. Since both $F_1$ and $F_2$ are proportional to the pressure intensity, the ratio $F_1/F_2$ is independent of this pressure and depends only on the dynamic mobility of the particles. Thus, the dynamic mobility can be determined from the ratio of $F_1/F_2$. In this way, the sensor 120 can be used for determining the dynamic mobility spectrum from measurements of the second kind of electroacoustic effect.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An apparatus for determining the particle charge and size distribution of particles in suspensions of arbitrary concentration, comprising:

at least two spaced apart electrodes in contact with a portion of the suspension;

means for generating one of two electroacoustic effects at a minimum of two different frequencies and means for measuring the resulting electroacoustic effect, including (a) means for applying an unsteady voltage difference to the electrodes thereby creating an unsteady electric field in the suspension to accelerate the particles and means for measuring the resulting acoustic wave generated by the particles in suspension under the action of the unsteady electric field; and (b) means for applying an unsteady mechanical force to the suspension in contact with the electrodes to accelerate the particles and means for measuring the resulting electrical response and acoustic pressure at the electrodes generated by the application of the unsteady mechanical force to the suspension;

means for measuring the acoustic properties of the suspension required for the determination of particle size and charge from the measured electroacoustic signal.

2. The apparatus of claim 1, further including a cell for mounting the electrodes and receiving the suspension.

3. The apparatus of claim 2, further including acoustic delay members wherein a portion of each member is in contact with the suspension and said portion in contact with the suspension having the electrodes physically bonded to the members and the acoustic transducers coupled to the delay members.

4. The apparatus of claim 3, wherein the delay members are elongated and the transducers are mounted on the ends opposite to the electrodes.

5. The apparatus of claim 3, wherein the means for measuring the acoustic properties of the suspension include a suspension transducer on one delay member mounted behind one of the electrodes facing the suspension for measuring the acoustic properties of the suspension.

6. The apparatus of claim 1, wherein the electrodes facing the suspension are made of a thin layer of a chemically inert conducting material.

7. The apparatus of claim 6, wherein the inert conducting material is gold.

8. The apparatus of claim 3, wherein the acoustic transducers are lithium niobate.

9. The apparatus of claim 3, wherein the acoustic delay members are glass rods.

10. The apparatus of claim 9, wherein the glass rods have a rectangular cross-section to avoid spurious acoustic signals.

11. The apparatus of claim 5, wherein the suspension transducer is a thin film of a piezoelectric material.

12. The apparatus of claim 1, wherein the electrodes are planar and the means for measuring the acoustic properties of the suspension include a suspension transducer disposed adjacent to one of the electrodes on the side away from the suspension.

13. The apparatus of claim 1, including the means for applying an unsteady voltage difference of at least two different frequencies to the electrodes and the means for measuring the resulting acoustic wave.

14. The apparatus of claim 4, wherein the elongated delay members are dimensioned so that the acoustic wave reaches the transducers after the unsteady electrical field is removed.

15. The apparatus of claim 1, including means for generating an unsteady mechanical force between the electrodes and means for measuring the resulting electrical response and acoustic pressure at the electrodes generated by application of the mechanical force.

16. An apparatus for determining the particle charge and size distribution of particles in suspensions of arbitrary concentration, comprising:
   at least two elongated acoustic delay members with one end of each member in contact with the suspension;
   at least one electrode physically bonded to the end of each delay member in contact with the suspension so that a portion of the suspension is between the electrodes;
   means for applying an unsteady voltage difference to the electrodes of at least two different frequencies for generating an unsteady electric field across a portion of the suspension to accelerate the particles in the suspension;
   means for measuring the resulting acoustic wave generated by the particles accelerated by the unsteady electric field in the suspension, including acoustic transducers coupled to the end of the delay members away from the suspension for generating an electrical signal in response to the acoustic wire; and
   means for measuring the acoustic properties of the suspension required for the determination of particle size and charge from the measured signal generated by the acoustic transducers.

17. The apparatus of claim 16, wherein the means for measuring the properties of the suspension include a suspension transducer mounted on one delay member behind one of the electrodes facing the suspension for measuring the acoustic properties of the suspension.

18. An apparatus for determining the particle charge and size distribution of particles in suspension of arbitrary concentration, comprising:
   at least two elongated acoustic delay members with one end of each member in contact with the suspension;
   at least one electrode physically bonded to the end of each delay member in contact with the suspension so that a portion of the suspension is between the electrodes;
   means for generating an unsteady mechanical force in the suspension between the electrodes of at least two different frequencies for accelerating the particles in suspension, including acoustic transducers coupled to the end of the delay members away from the suspension for generating the unsteady mechanical force in the suspension between the electrodes;
   means for measuring the resulting electrical response and acoustic pressure at the electrodes in contact with the suspension due to the unsteady mechanical force generated in the suspension by the acoustic transducers coupled to the delay members; and
   means for measuring the acoustic properties of the suspension required for the determination of particle size and charge from the measured electrical response and acoustic pressure at the electrodes.

19. The apparatus of claim 18, wherein the means for measuring the acoustic properties of the suspension include a suspension transducer mounted on one delay member behind one of the electrodes facing the suspension.

20. The apparatus of claim 11, wherein the piezoelectric material is a polymer including polyvinylidene fluoride.

* * * * *